United States Patent
Kim et al.

(10) Patent No.: US 10,487,053 B2
(45) Date of Patent: Nov. 26, 2019

(54) ACID ADDITION SALT OF 1-(5-(2,4-DIFLUOROPHENYL)-1-((3-FLUOROPHENYL)SULFONYL)-4-METHOXY-1H-PYRROL-3-YL)-N-METHYLMETHANAMINE

(71) Applicant: Daewoong Pharmaceutical Co., Ltd., Gyeonggi-do (KR)

(72) Inventors: Aeri Kim, Seoul (KR); Kwan Hyung Cho, Busan (KR)

(73) Assignee: Daewoong Pharmaceutical Co., Ltd., Gyeonggi-do (KR)

( * ) Notice: Subject to any disclaimer, the term of this patent is extended or adjusted under 35 U.S.C. 154(b) by 0 days.

(21) Appl. No.: 16/073,388

(22) PCT Filed: Mar. 17, 2017

(86) PCT No.: PCT/KR2017/002913
§ 371 (c)(1),
(2) Date: Jul. 27, 2018

(87) PCT Pub. No.: WO2017/164575
PCT Pub. Date: Sep. 28, 2017

(65) Prior Publication Data
US 2019/0031609 A1    Jan. 31, 2019

(30) Foreign Application Priority Data

Mar. 25, 2016 (KR) .................. 10-2016-0036081
Feb. 9, 2017 (KR) .................. 10-2017-0018336

(51) Int. Cl.
*C07D 207/48* (2006.01)
*C07C 55/10* (2006.01)
*C07C 57/15* (2006.01)
*C07C 59/255* (2006.01)
*A61P 1/04* (2006.01)

(52) U.S. Cl.
CPC .............. *C07D 207/48* (2013.01); *A61P 1/04* (2018.01); *C07C 55/10* (2013.01); *C07C 57/15* (2013.01); *C07C 59/255* (2013.01)

(58) Field of Classification Search
CPC ............................. C07D 207/48; C07C 55/10
See application file for complete search history.

(56) References Cited

U.S. PATENT DOCUMENTS

| 8,048,909 | B2 | 11/2011 | Kajino et al. |
| 8,338,461 | B2 | 12/2012 | Kajino et al. |
| 8,436,187 | B2 | 5/2013 | Kajino et al. |
| 10,100,010 | B1 * | 10/2018 | Lee .................. C07D 207/48 |
| 2010/0113524 | A1 | 5/2010 | Garst et al. |
| 2011/0288040 | A1 | 11/2011 | Hasuoka et al. |
| 2015/0307449 | A1 | 10/2015 | Lan et al. |

FOREIGN PATENT DOCUMENTS

| CN | 104447491 A | 3/2015 |
| EP | 1803709 A1 | 7/2007 |
| JP | 2008-522952 A | 7/2008 |
| KR | 10-2007-0060133 | 6/2007 |
| KR | 10-1613245 B1 | 4/2016 |
| RU | 2415838 C2 | 4/2011 |
| WO | WO-2016/175555 A2 | 11/2016 |

OTHER PUBLICATIONS

International Search Report and Written Opinion in International Application No. PCT/KR2017/002913 dated Jun. 29, 2017, 11 pages.
Rabon et al., Preparation of Gastric $H^+$, $K^+$ -ATPase, Methods in Enzymology, vol. 157, Academic Press Inc. 1988, pp. 649-654.
Notice of Acceptance for Patent Application in AU Application No. 2017238917 dated Jul. 2, 2019, 3 pages.
Extended European Search Report in EP Application No. 17770545.6 dated Jul. 3, 2019, 6 pages.
Notice of Reasons for Refusal in JP Application No. 2018-549922 dated Jun. 25, 2019, 4 pages.
Blangetti et al., "LIC-KOR-Promoted Synthesis of Alkoxydienyl Amines: An Entry to 2,3,4,5-Tetrasubstituted Pyrroles", Organic Letters, vol. 11, No. 17, 2009, pp. 3914-3917.

* cited by examiner

*Primary Examiner* — Golam M Shameem
(74) *Attorney, Agent, or Firm* — Marshall, Gerstein & Borun LLP

(57) ABSTRACT

The present invention provides a novel acid addition salt of 1-(5-(2,4-difluorophenyl)-1-((3-fluorophenyl)sulfonyl)-4-methoxy-1H-pyrrol-3-yl)-N-methylmethanamine. The above-described acid addition salt can have not only excellent proton pump inhibitory activity, gastric damage inhibitory activity and defensive factor-enhancing effect, but also excellent eradication activity against *H. pylori* and thus can be effectively used for the prevention and treatment of gastrointestinal injury due to gastrointestinal track ulcer, gastritis, reflux esophagitis, or *H. pylori*.

5 Claims, No Drawings

ACID ADDITION SALT OF 1-(5-(2,4-DIFLUOROPHENYL)-1-((3-FLUOROPHENYL)SULFONYL)-4-METHOXY-1H-PYRROL-3-YL)-N-METHYLMETHANAMINE

TECHNICAL FIELD

The present invention relates to a novel acid addition salt of 1-(5-(2,4-difluorophenyl)-1-((3-fluorophenyl)sulfonyl)-4-methoxy-1H-pyrrol-3-yl)-N-methylmethanamine.

BACKGROUND OF ART

The selection of pharmaceutically acceptable salts is a critical step in the process for researching and developing new medicines. This is because salts of certain medicines can often be important determinants of ease of preparation of medicine raw materials, solubility, stability during distribution and storage, ease of formulation and pharmacokinetic properties.

The production of various kinds of salts can be a means of changing the physiochemical and biological properties of the medicines without altering the chemical structure of the specific medicines. Upon selecting a preferred salt, the properties of many salts must be considered. For example, it can be taken into consideration depending on the environment and the situation where various factors such as ease of production, stability, solubility, and/or hygroscopicity of salt are used.

In particular, there is a continuing need for drug formulations that exhibit better bioavailability or better stability, and thus continuous research for novel salts or purer salts of existing medicine molecules has been conducted.

Thus, the present inventors have found that a novel acid addition salt of 1-(5-(2,4-difluorophenyl)-1-((3-fluorophenyl)sulfonyl)-4-methoxy-1H-pyrrol-3-yl)-N-methylmethanamine which is a new active medicinal substance can be prepared and they can be pharmaceutically used based on their physicochemical properties and stabilities, thereby completing the present invention.

DETAILED DESCRIPTION OF THE INVENTION

Technical Problem

It is an object of the present invention to provide a pharmaceutically acceptable acid addition salt of 1-(5-(2,4-difluorophenyl)-1-((3-fluorophenyl)sulfonyl)-4-methoxy-1H-pyrrol-3-yl)-N-methylmethanamine which has high solubility in water and excellent stability.

Technical Solution

In order to achieve the above object, the present invention provides:
1-(5-(2,4-difluorophenyl)-1-((3-fluorophenyl)sulfonyl)-4-methoxy-1H-pyrrol-3-yl)-N-methylmethanamine hydrochloride,
1-(5-(2,4-difluorophenyl)-1-((3-fluorophenyl)sulfonyl)-4-methoxy-1H-pyrrol-3-yl)-N-methylmethanamine succinate,
1-(5-(2,4-difluorophenyl)-1-((3-fluorophenyl)sulfonyl)-4-methoxy-1H-pyrrol-3-yl)-N-methylmethanamine tartrate, and
1-(5-(2,4-difluorophenyl)-1-((3-fluorophenyl)sulfonyl)-4-methoxy-1H-pyrrol-3-yl)-N-methylmethanamine fumarate.

Hereinafter, the present invention will be described in detail.

A 1-(5-(2,4-difluorophenyl)-1-((3-fluorophenyl)sulfonyl)-4-methoxy-1H-pyrrol-3-yl)-N-methylmethanamine, which is a new active medicinal substance, is a compound represented by the following chemical formula(1), which corresponds to a 4-methoxypyrrole derivative:

[Chemical Formula 1]

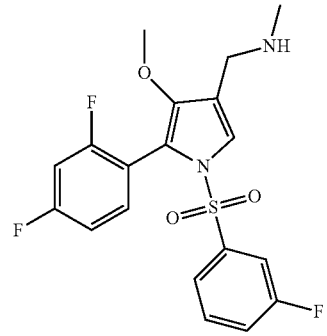

The above 1-(5-(2,4-difluorophenyl)-1-((3-fluorophenyl)sulfonyl)-4-methoxy-1H-pyrrol-3-yl)-N-methyl methanamine and a pharmaceutically acceptable salt thereof can have not only a proton pump inhibitory activity, a gastric damage inhibitory activity and a defensive factor-enhancing effects, but also excellent eradication activity against *Helicobacter pylori*(*H. pylori*). Therefore, the 1-(5-(2,4-difluorophenyl)-1-((3-fluorophenyl)sulfonyl)-4-methoxy-1H-pyrrol-3-yl)-N-methylmethanamine and a pharmaceutically acceptable salt thereof can be effectively used for the prevention and treatment of gastrointestinal injury due to gastrointestinal tract ulcer, gastritis, reflux esophagitis, or *H. pylori*.

The pharmaceutically acceptable salt of 1-(5-(2,4-difluorophenyl)-1-((3-fluorophenyl)sulfonyl)-4-methoxy-1H-pyrrol-3-yl)-N-methylmethanamine can be an acid addition salt of 1-(5-(2,4-difluorophenyl)-1-((3-fluorophenyl)sulfonyl)-4-methoxy-1H-pyrrol-3-yl)-N-methylmethanamine.

In this case, the acid may be hydrochloric acid, succinic acid, tartaric acid, or fumaric acid.

The acid addition salt of 1-(5-(2,4-difluorophenyl)-1-((3-fluorophenyl)sulfonyl)-4-methoxy-1H-pyrrol-3-yl)-N-methylmethanamine can be prepared by a preparation method comprising the steps of:

1) dissolving 1-(5-(2,4-difluorophenyl)-1-((3-fluorophenyl)sulfonyl)-4-methoxy-1H-pyrrol-3-yl)-N-methylmethanamine and an acid, respectively, in an organic solvent to prepare a 1-(5-(2,4-difluorophenyl)-1-((3-fluorophenyl)sulfonyl)-4-methoxy-1H-pyrrol-3-yl)-N-methylmethanamine solution and an acid solution; and
2) mixing the 1-(5-(2,4-difluorophenyl)-1-((3-fluorophenyl)sulfonyl)-4-methoxy-1H-pyrrol-3-yl)-N-methylmethanamine solution and the acid solution and then stirring the mixed solutions.

The step 1) is a step of preparing the respective solutions using a good solvent capable of completely dissolving 1-(5-(2,4-difluorophenyl)-1-((3-fluorophenyl)sulfonyl)-4-methoxy-1H-pyrrol-3-yl)-N-methylmethanamine and an acid, respectively, and the solvents used in dissolving 1-(5-(2,4-difluorophenyl)-1-((3-fluorophenyl)sulfonyl)-4-methoxy-1H-pyrrol-3-yl)-N-methylmethanamine and an acid may be the same or different.

In this case, as the acid, hydrochloric acid, succinic acid, tartaric acid, or fumaric acid may be used.

Further, the organic solvent may be one or more selected from the group consisting of n-hexane, ethyl acetate, butyl acetate, acetonitrile, chloroform, diethyl ether, acetone, methanol and ethanol.

Specifically, in the step of preparing a 1-(5-(2,4-difluorophenyl)-1-((3-fluorophenyl)sulfonyl)-4-methoxy-1H-pyrrol-3-yl)-N-methylmethanamine solution, the organic solvent can be used as a volume (ml/g) of 1-20 times, or preferably as a volume(ml/g) of 1-10 times, relative to the weight of the 1-(5-(2,4-difluorophenyl)-1-((3-fluorophenyl)sulfonyl)-4-methoxy-1H-pyrrol-3-yl)-N-methylmethanamine.

Further, in the step of preparing an acid solution, the organic solvent can be used as a volume (ml/g) of 1-30 times, or preferably as a volume (ml/g) of 5-30 times, relative to the weight of the acid.

The step 2) is a step of mixing the solutions prepared in the step 1) and then stirring the mixed solutions to produce a salt in which 1-(5-(2,4-difluorophenyl)-1-((3-fluorophenyl)sulfonyl)-4-methoxy-1H-pyrrol-3-yl)-N-methylmethanamine and an acid are chemically bonded.

In this case, in the step of mixing the prepared solutions, the acid can be used in 0.5 to 3 equivalents or preferably in 0.5 to 2 equivalents, relative to the 1-(5-(2,4-difluorophenyl)-1-((3-fluorophenyl)sulfonyl)-4-methoxy-1H-pyrrol-3-yl)-N-methylmethanamine. Within the above range, a salt in which 1-(5-(2,4-difluorophenyl)-1-((3-fluorophenyl)sulfonyl)-4-methoxy-1H-pyrrol-3-yl)-N-methylmethanamine and an acid are bonded in a molar ratio of 1:0.5, 1:1, 1:1.5, or 1:2 can be produced.

Next, the step of stirring the mixed solutions can be carried out at a temperature of 24° C. to 28° C. for 30 minutes to 4 hours. At this time, the stirring speed may be in the range of 50 rpm to 300 rpm. Within this range, salts with high yield and high purity can be produced.

The acid addition salt of 1-(5-(2,4-difluorophenyl)-1-((3-fluorophenyl)sulfonyl)-4-methoxy-1H-pyrrol-3-yl)-N-methylmethanamine prepared by the above preparation method can be recovered from the solution by the vacuum filtration method. If necessary, the recovered acid addition salt was washed and dried under vacuum to obtain an acid addition salt with high purity. In addition, the reaction conditions such as the ratio of solvent, the temperature range, the process time, and the like described in the above preparation method can be adjusted depending on the selected solvent.

On the other hand, the present invention provides a pharmaceutical composition for the prevention and treatment of gastrointestinal injury due to gastrointestinal tract ulcer, gastritis, reflux esophagitis, or *H. pylori*, comprising one or more acid addition salts selected from the group consisting of hydrochloride, succinate, tartrate and fumarate of 1-(5-(2,4-difluorophenyl)-1-((3-fluorophenyl)sulfonyl)-4-methoxy-1H-pyrrol-3-yl)-N-methylmethanamine.

Such pharmaceutical composition may include pharmaceutically acceptable carriers that are commonly used. The carrier be one that is usually used at the time of formulation, and it includes lactose, dextrose, sucrose, sorbitol, mannitol, starch, gum acacia, calcium phosphate, alginate, gelatin, calcium silicate, microcrystalline cellulose, polyvinylpyrrolidone, cellulose, water, syrup, methyl cellulose, methyl hydroxybenzoate, propyl hydroxybenzoate, talc, magnesium stearate, mineral oil and the like, but are not limited thereto. The pharmaceutical composition may further include a lubricant, a wetting agent, a sweetener, a flavoring agent, an emulsifying agent, a suspending agent, a preservative, etc. in addition to the above components.

The pharmaceutical composition may be administered orally, or administered parenterally, including intravenous, intramuscular, intraperitoneal, subcutaneous and transdermal routes of administration.

In this case, the pharmaceutical composition may be administered in a therapeutically effective amount, for example, in an effective amount ranging about 0.001 mg/kg to about 100 mg/kg per day. The dosage may vary depending on formulation method, administration method, patient's age, body weight, sexually transmitted infection, diet, administration time, administration route, excretion rate or susceptibility.

The pharmaceutical composition can be formulated by the method that can be performed easily by those in the art by using a pharmaceutically acceptable carrier and/or excipient in the form of unit dose or in multi-dose container. In this case, the formulation can be used without limitation as long as it is in any form suitable for pharmaceutical preparations including oral dosage forms such as powders, granules, tablets, capsules, suspensions, emulsions, syrups or aerosols, external preparations such as ointments or creams, suppositories and sterilized injection solutions. In addition, a dispersing agent or a stabilizer can be further included.

Advantageous Effects

The acid addition salts of 1-(5-(2,4-difluorophenyl)-1-((3-fluorophenyl)sulfonyl)-4-methoxy-1H-pyrrol-3-yl)-N-methylmethanamine according to the present invention have high solubility in water and excellent stability under moisture-proof conditions and high-humidity exposure conditions, and thus can be pharmaceutically used.

DETAILED DESCRIPTION OF THE EMBODIMENTS

Below, preferred embodiments will be provided in order to assist in the understanding of the present disclosure. However, these examples are provided only for illustration of the present invention, and should not be construed as limiting the present invention to these examples.

Preparation Example

Preparation of 1-(5-(2,4-difluorophenyl)-1-((3-fluorophenyl)sulfonyl)-4-methoxy-1H-pyrrol-3-yl)-N-methylmethanamine (Free Base)

Step 1-1) Preparation of 2-(2,4-difluorophenyl)-2-((3-methoxy-2-(methoxycarbonyl)-3-oxoprop-1-en-1-yl)amino)acetic acid 2,4-Difluorophenyl glycine (150.0 g, 801.5 mmol), dimethyl 2-(methoxymethylene)malonate (126.9 g, 728.6 mmol) and sodium acetate (65.8 g, 801.5 mmol) were added to methanol (800.0 ml), and the mixture was then refluxed at 60° C. for 4 hours. The reaction mixture was cooled to room temperature and then concentrated under reduced pressure to remove about 70% of methanol, and then filtered. The obtained solid was dried under reduced pressure to give 190.0 g of the title compound. (Yield: 79.2%).

$^1$H-NMR (500 MHz, CDCl$_3$): 8.02-7.99 (m, 1H), 7.45-7.40 (m, 1H), 7.00-6.95 (m, 2H), 5.16 (s, 1H), 3.74 (s, 3H), 3.76 (s, 3H)

Step 1-2) Preparation of methyl 5-(2,4-difluorophenyl)-4-hydroxy-1H-pyrrol-3-carboxylate Acetic anhydride (1731.2 ml) and triethylamine (577.1 ml) were added to 2-(2,4-difluorophenyl)-2-((3-methoxy-2-(methoxycarbonyl)-3-oxoprop-1-en-1-yl)amino)acetic acid (190.0 g, 577.1 mmol) prepared in the step 1-1. The reaction mixture was refluxed at 140° C. for 30 minutes and then cooled to 0° C. To the reaction mixture, ice water (577.1 ml) was added at 0° C., stirred at room temperature for 1 hours and then extracted with ethyl acetate. The obtained extract was dried over anhydrous magnesium sulfate, and concentrated under reduced pressure. The resulting compound was filtered using silica gel to remove solids, and then concentrated under reduced pressure.

Tetrahydrofuran (140.0 ml) and water (120.0 ml) were added to the resulting residue, and the mixture was cooled at 0° C. and sodium hydroxide (46.17 g, 1154.2 mmol) was then added thereto. The reaction mixture was stirred at 0° C. for 30 minutes, neutralized with 1N aqueous hydrochloric acid solution and then extracted with ethyl acetate. The obtained extract was dried over anhydrous magnesium sulfate, and then concentrated under reduced pressure. The resulting residue was purified by silica gel column chromatography (ethyl acetate:n-hexane=1:4 (v/v)) to give 22.0 g of the title compound. (Yield: 15.1%).

$^1$H-NMR (500 MHz, CDCl$_3$): 8.80 (s, 1H), 8.17-8.12 (m, 2H), 7.13 (d, 1H), 6.95 (t, 1H), 6.86-6.83 (m, 1H), 3.88 (s, 3H)

Step 1-3) Preparation of methyl 5-(2,4-difluorophenyl)-4-methoxy-1H-pyrrol-3-carboxylate Methyl 5-(2,4-difluorophenyl)-4-hydroxy-1H-pyrrol-3-carboxylate (22.0 g, 86.9 mmol) prepared in the step 1-2 was dissolved in tetrahydrofuran (434.5 ml) and methanol (173.9 ml). To the reaction mixture, (trimethylsilyl)diazomethane (2.0 M diethyl ether solution, 173.8 ml) was added, and stirred at room temperature for 48 hours. Water was added to the reaction mixture and extracted with ethyl acetate. The obtained extract was dried over anhydrous magnesium sulfate, and concentrated under reduced pressure. The resulting residue was purified by silica gel column chromatography (ethyl acetate:n-hexane=1:4 (v/v)) to give 18.1 g of the title compound. (Yield: 75.3%)

$^1$H-NMR (500 MHz, CDCl$_3$): 8.78 (s, 1H), 8.12 (m, 1H), 7.30 (d, 1H), 6.95 (t, 1H), 6.88 (t, 1H), 3.87 (s, 3H), 3.85 (s, 3H)

Step 1-4) Preparation of methyl 5-(2,4-difluorophenyl)-4-methoxy-1-((3-fluorophenyl)sulfonyl)-IH-pyrrol-3-carboxylate Methyl 5-(2,4-difluorophenyl)-4-methoxy-1H-pyrrol-3-carboxylate (18.0 g, 67.4 mmol) prepared in the step 1-3 was dissolved in dimethylformamide (335.0 ml). To the obtained solution, sodium hydride (60%, dispersion in liquid paraffin) (4.0 g, 101.0 mmol) was added at room temperature and the mixture was stirred at room temperature for 10 minutes. To the reaction mixture, 3-fluorobenzenesulfonyl chloride (13.37 ml, 101.0 mmol) was added, and the mixture was stirred at room temperature for 1 hour. Water was added to the reaction mixture and extracted with ethyl acetate. The obtained extract was dried over anhydrous magnesium sulfate, and then concentrated under reduced pressure. The resulting residue was purified by silica gel column chromatography (ethyl acetate:n-hexane=1:4 (v/v)) to give the title compound (26.1 g). (Yield: 91.1%).

$^1$H-NMR (500 MHz, CDCl$_3$): 7.98 (s, 1H), 7.43-7.39 (m, 1H), 7.30 (t, 1H), 7.23 (d, 1H), 7.15 (q, 1H), 7.67 (q, 1H), 6.91 (t, 1H), 6.77 (t, 1H), 3.87 (s, 3H), 3.61 (s, 3H)

Step 1-5) Preparation of 5-(2,4-difluorophenyl)-4-methoxy-1-((3-fluorophenyl)sulfonyl)-IH-pyrrol-3-carbaldehyde Methyl 5-(2,4-difluorophenyl)-4-methoxy-1-((3-fluorophenyl)sulfonyl)-IH-pyrrol-3-carboxylate (26.0 g, 61.1 mmol) prepared in the step 1-4 was dissolved in tetrahydrofuran (300.0 ml). Diisobutyl aluminum hydride (1.0 M tetrahydrofuran solution) (183.4 ml, 183.4 mmol) was added to the obtained solution at 0° C., and the mixture was stirred at room temperature for 1 hour, neutralized with 1N hydrochloric acid solution and then extracted with ethylacetate. The obtained extract was dried over anhydrous magnesium sulfate, and then concentrated under reduced pressure.

The resulting residue was dissolved in dichloromethane (300.0 ml), and then celite (26.0 g) and pyridinium chlorochromate (39.5 g, 183.4 mmol) were added thereto. The reaction mixture was stirred at room temperature for 1 hour and then filtered to remove a solid, and the obtained filtrate was concentrated under reduced pressure. The resulting residue was purified by silica gel column chromatography (ethyl acetate:n-hexane=1:2 (v/v)) to give the title compound (17.2 g). (Yield: 70.9%).

$^1$H-NMR (500 MHz, CDCl$_3$): 9.89 (s, 1H), 7.99 (s, 1H), 7.45-7.41 (m, 1H), 7.33 (s, 1H), 7.25 (d, 1H), 7.18 (q, 1H), 7.05 (s, 1H), 6.92 (t, 1H), 6.77 (t, 1H), 3.63 (s, 3H)

Step 1-6) Preparation of 1-(5-(2,4-difluorophenyl)-4-methoxy-1-((3-fluorophenyl)sulfonyl)-IH-pyrrol-3-yl)-N-methylmethanamine 5-(2,4-difluorophenyl)-4-methoxy-1-((3-fluorophenyl)sulfonyl)-IH-pyrrol-3-carbaldehyde (17.0 g, 43.0 mmol) prepared in the step 1-5 was dissolved in methanol (430.0 ml). Methylamine (9.8 M methanol solution) (87.8 ml, 860.0 mmol) was added to the obtained solution, and the mixture was stirred at room temperature for 30 minutes. Sodium borohydride (16.3 g, 430.0 mmol) was added to the reaction mixture, and the mixture was stirred at room temperature for 30 minutes. Water was added to the reaction mixture and extracted with ethyl acetate. The obtained extract was dried over anhydrous magnesium sulfate, and then concentrated under reduced pressure. The resulting residue was purified by silica gel column chromatography (ethyl acetate:n-hexane=1:2 (v/v)) to give the title compound (15.2 g). (Yield: 86.1%).

$^1$H-NMR (500 MHz, CDCl$_3$): 7.39-7.35 (m, 1H), 7.26-7.20 (m, 2H), 7.15 (q, 1H), 7.06 (d, 1H), 6.87 (t, 1H), 6.78 (t, 1H), 3.60 (d, 2H), 3.44 (s, 3H), 2.45 (s, 3H)

Hereinafter, in the following examples, 1-(5-(2,4-difluorophenyl)-4-methoxy-1-((3-fluorophenyl)sulfonyl)-IH-pyrrol-3-yl)-N-methylmethanamine (free base) prepared in Preparation Example was used.

Example 1: Preparation of 1-(5-(2,4-difluorophenyl)-1-((3-fluorophenyl)sulfonyl)-4-methoxy-1H-pyrrol-3-yl)-N-methylmethanamine hydrochloride

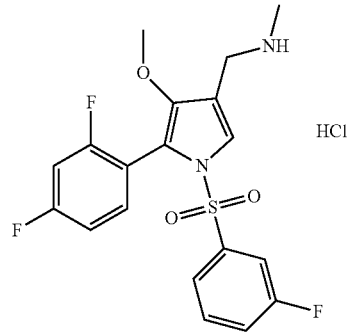 [SMILES: CNCc1cn(S(=O)(=O)c2cccc(F)c2)c(-c2ccc(F)cc2F)c1OC ; Cl]

1-(5-(2,4-difluorophenyl)-4-methoxy-1-((3-fluorophenyl)sulfonyl)-IH-pyrrol-3-yl)-N-methylmethanamine (15.0 g, 36.6 mmol) prepared in Preparation Example was dissolved in ethyl acetate (36.6 ml) to which hydrochloric acid solution (2.0 M diethyl ether solution) (36.6 ml, 73.1 mmol) was added. The reaction mixture was stirred at room temperature for 1 hour and then filtered, and the obtained solid was dried under reduced pressure to give the title compound (15.1 g). (Yield: 92.5%).

Molecular weight 446.87

$^1$H-NMR (500 MHz, MeOD): 7.69 (s, 1H), 7.58-7.53 (m, 1H), 7.45 (t, 1H), 7.30 (d, 1H), 7.20-7.15 (m, 2H), 7.02-6.94 (m, 2H), 4.07 (d, 2H), 3.46 (s, 3H), 2.71 (s, 3H)

The compounds of the following additional examples are prepared by a method similar to the preparation method of the Example above, except that the starting materials were suitably replaced to comply with the structure of the compounds to be prepared with reference to the preparation methods within the present disclosure.

Example 2: Preparation of 1-(5-(2,4-difluorophenyl)-1-((3-fluorophenyl)sulfonyl)-4-methoxy-1H-pyrrol-3-yl)-N-methylmethanamine succinate

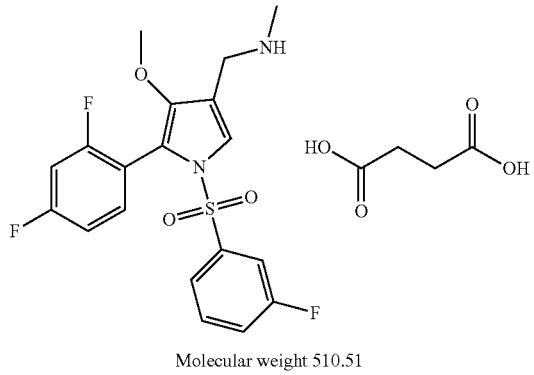 [SMILES: CNCc1cn(S(=O)(=O)c2cccc(F)c2)c(-c2ccc(F)cc2F)c1OC ; O=C(O)CCC(=O)O]

Molecular weight 510.51

$^1$H-NMR (500 MHz, MeOD): 7.60 (s, 1H), 7.57-7.52 (m, 1H), 7.46-7.43 (t, 1H), 7.30 (d, 1H), 7.19-7.14 (m, 2H), 7.01-6.94 (m, 2H), 3.91 (s, 2H), 3.45 (s, 3H), 2.59 (s, 3H), 2.50 (s, 2H)

Example 3: Preparation of 1-(5-(2,4-difluorophenyl)-1-((3-fluorophenyl)sulfonyl)-4-methoxy-1H-pyrrol-3-yl)-N-methylmethanamine tartrate

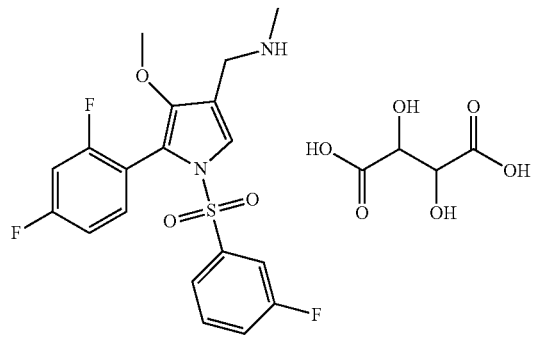

Molecular weight 560.50

$^1$H-NMR (500 MHz, MeOD): 7.70 (s, 1H), 7.58-7.53 (m, 1H), 7.49-7.44 (t, 1H), 7.31 (d, 1H), 7.20-7.15 (m, 2H), 7.03-6.94 (m, 2H), 4.4 (s, 2H), 4.07 (s, 2H), 3.46 (s, 3H), 2.71 (s, 3H)

Example 4: Preparation of 1-(5-(2,4-difluorophenyl)-1-((3-fluorophenyl)sulfonyl)-4-methoxy-1H-pyrrol-3-yl)-N-methylmethanamine fumarate

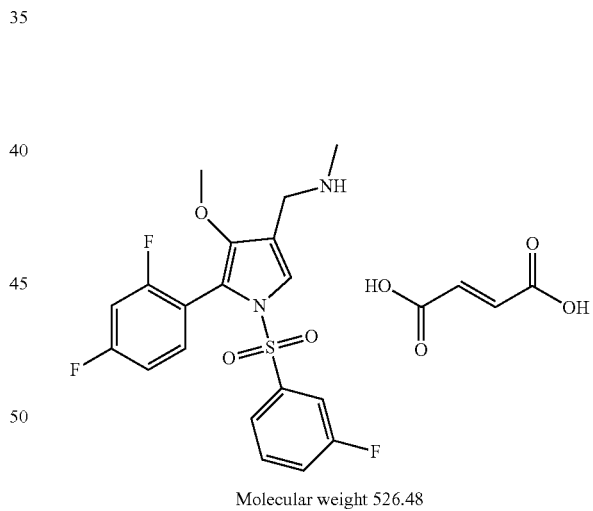

Molecular weight 526.48

$^1$H-NMR (500 MHz, MeOD): 7.63 (s, 1H), 7.58-7.53 (m, 1H), 7.48-7.44 (t, 1H), 7.30 (d, 1H), 7.20-7.16 (m, 2H), 7.02-6.94 (m, 2H), 6.68 (s, 1H), 3.97 (s, 2H), 3.45 (s, 3H), 2.64 (s, 3H)

Test Example 1: Inhibitory Effects on Proton Pump (H$_+$/K$_+$-ATPase) Activity

The inhibitory effects on proton pump ((H$_+$/K$_+$-ATPase) activity of 1-(5-(2,4-difluorophenyl)-1-((3-fluorophenyl)

sulfonyl)-4-methoxy-1H-pyrrol-3-yl)-N-methylmethan-amine hydrochloride prepared in Example 1 were measured as follows.

Gastric vesicles were prepared from a hog stomach according to a known method (Edd C. Rabon et al., Preparation of Gastric ($H_+,K_+$-ATPase., Methods in enzymology, vol. 157 Academic Press Inc., (1988), pp. 649-654). The protein contents of gastric vesicles thus prepared were quantitatively measured with Bicinchoninic Acid (BCA) kit (Thermo). 80 μl of (a predetermined concentration of a test compound, 0.5% DMSO, 2.5 mM $MgCl_2$, 12.5 mM KCl, 1.25 mM EDTA, 60 mM Tris-HCl, pH7.4) was added to each well of 96-well plates. 10 μl of a reaction solution containing gastric vesicles (60 mmol/l, Tris-HCl buffer, pH 7.4) and 10 μl of a Tris buffer solution containing adenosine triphosphate (10 mM ATP, Tris-HCl buffer solution, pH 7.4) were added to each well and subjected to enzymatic reaction at 37° C. for 40 minutes. 50 μl of malachite green solution (0.12% malachite green solution in 6.2 N sulfuric acid, 5.8% ammonium molybdate and 11% Tween 20 were mixed at a ratio of 100:67:2) was added thereto to stop the enzyme reaction, and 50 μl of 15.1% sodium citrate was added thereto. The amount of monophosphate(Pi) in the reaction solution was measured at 570 nm by using a microplate reader (FLUOstar Omega, BMG). The inhibition rate (%) was measured from the activity value of the control group and the activity value of the test compounds at various concentrations. The concentration ($IC_{50}$) that inhibits $H_+/K_+$-ATPase activity by 50% was calculated from each % inhibition value of the compounds using Logistic 4-parameter function of Sigmaplot 8.0 program.

As a result, 1-(5-(2,4-difluorophenyl)-1-((3-fluorophenyl)sulfonyl)-4-methoxy-1H-pyrrol-3-yl)-N-methylmethan-amine hydrochloride prepared in Example 1 exhibited an $IC_{50}$ value of 0.024 μM. Thus, an acid addition salt of 1-(5-(2,4-difluorophenyl)-1-((3-fluorophenyl)sulfonyl)-4-methoxy-1H-pyrrol-3-yl)-N-methylmethanamine according to one embodiment of the present invention had excellent proton pump inhibitory activity and thus can be used for a pharmaceutical composition for the prevention and treatment of gastrointestinal injury due to gastrointestinal tract ulcer, gastritis, reflux esophagitis, or *H. pylori*.

Test Example 2: Hygroscopicity Test

The hygroscopicity test was carried out for the acid addition salts prepared in the above Examples. First, 40 mg of the salts of the Examples were tightly sealed and stored in each glass desiccator containing a saturated aqueous solution of several salts for at least two days under the condition of constant relative humidity as shown in Table 1 below. Subsequently, the result of measurement of weight change for each of these salts showed that weight change due to moisture was not observed. Accordingly, it could be seen that the acid addition salts prepared in the Examples did not have hygroscopicity.

TABLE 1

| Desiccator | Relative humidity | Types of salt-saturated aqueous solution |
|---|---|---|
| 1 | 33% | $MgCl_2$-saturated aqueous solution |
| 2 | 53% | $Mg(NO_3)_2 \cdot 6H_2O$-saturated aqueous solution |
| 3 | 64% | $NaNO_2$-saturated aqueous solution |
| 4 | 75% | NaCl-saturated aqueous solution |
| 5 | 93% | $KNO_3$-aqueous solution |

Test Example 3: Stability Confirmation Test

The stability test was carried out for the acid addition salts prepared in the Examples to evaluate the degree to which impurities were formed during storage under severe conditions (moisture-proof condition and high-humidity exposure condition). The results of the stability test under the moisture-proof condition were shown in Table 2 below, and the results of the stability test under the high-humidity exposure condition were shown in Table 3 below.

For the stability test, vials containing 10 mg of each sample which was precisely weighed and taken were prepared in the planned quantity, and they were stored by dividing into the moisture-proof condition (60° C. and less than 10% relative humidity) and under the high-humidity exposure condition (60° C. and 95% relative humidity). However, under the high-humidity exposure condition, a stopper of the vial was not used to keep so that the sample is in sufficient contact with a moisture in the air. At a fixed point of time after the initiation of the test, two vials per point of time were taken (number of samples per test n=2). 10 ml of methanol was added to each vial to dissolve the sample, which was then centrifuged. The resulting supernatant was analyzed using a liquid chromatography. The peak area was determined by integration for all detected peaks, and the relative peak area for the main component and the total impurity was calculated and expressed as an average value.

TABLE 2

| | | Initial | | After 2 weeks | | After 4 weeks | |
|---|---|---|---|---|---|---|---|
| | Types of salt | Peak area of main component (%) | Peak area of total impurities (%) | Peak area of main component (%) | Peak area of total impurities (%) | Peak area of main component (%) | Peak area of total impurities (%) |
| Example 1 | Hydrochloride | 99.82 | 0.18 | 99.80 | 0.19 | 99.80 | 0.20 |
| Example 2 | Succinate | 99.55 | 0.45 | 99.61 | 0.39 | 99.55 | 0.45 |
| Example 3 | Tartrate | 99.52 | 0.48 | 99.54 | 0.46 | 99.48 | 0.52 |
| Example 4 | Fumarate | 99.38 | 0.62 | 99.36 | 0.64 | 99.37 | 0.63 |

TABLE 3

| | | Initial | | After 1 week | | After 2 weeks | | After 4 weeks | |
|---|---|---|---|---|---|---|---|---|---|
| | Type of salt | Peak area of main component (%) | Peak area of total impurities (%) | Peak area of main component (%) | Peak area of total impurities (%) | Peak area of main component (%) | Peak area of total impurities (%) | Peak area of main component (%) | Peak area of total impurities (%) |
| Example 1 | Hydrochloride | 99.82 | 0.18 | 99.81 | 0.19 | 99.80 | 0.20 | 99.80 | 0.20 |
| Example 2 | Succinate | 99.55 | 0.45 | 99.56 | 0.44 | 99.53 | 0.47 | 99.47 | 0.54 |
| Example 3 | Tartrate | 99.52 | 0.48 | 99.48 | 0.52 | 99.43 | 0.57 | 99.23 | 0.77 |
| Example 4 | Fumarate | 99.38 | 0.62 | 99.40 | 0.60 | 99.32 | 0.68 | 99.30 | 0.70 |

As shown in Tables 2 and 3, it could be confirmed that the acid addition salts prepared in the Examples did not show a decrease in the peak area of the main component and an increase in the peak area of the total impurities which were significant under the moisture-proof condition and the high-humidity exposure condition. Therefore, it was confirmed that the acid addition salts prepared in the Examples suppressed an increase of impurities regardless of the influence of humidity under severe conditions and exhibited excellent chemical stability.

Test Example 4: Solubility Test in Water

The solubility test in water was carried out for the acid addition salts prepared in the Examples, and the results were shown in Table 4 below. For the solubility test in water, a sample of less than 10 mg was first precisely weighed and taken, and placed into a vial, to which 50 μl of deionized water was added, shaking for 30 seconds and ultrasonic shaking for 1 minute were carried out, and these processes were repeated several times. The water solubility was calculated by measuring the amount of water used to dissolve all the samples.

TABLE 4

| | Type of Salts | Solubility in water (mg/ml) |
|---|---|---|
| Example 1 | Hydrochloride | 11.11 |
| Example 2 | Succinate | 7.20 |
| Example 3 | Tartrate | 6.90 |
| Example 4 | Fumarate | 1.73-2.60 |
| Preparation Example | Free base | Less than 0.16 |

As shown in Table 4, it could be confirmed that the acid addition salts prepared in the Examples had a water solubility of 10 times or more as compared with that of the free base prepared in Preparation Example. In addition, the acid addition salts prepared in the Examples showed high solubility in the order of hydrochloride, succinate, tartrate and fumarate.

What is claimed is:

1. An acid addition salt of 1-(5-(2,4-difluorophenyl)-1-((3-fluorophenyl)sulfonyl)-4-methoxy-1H-pyrrol-3-yl)-N-methylmethanamine wherein the acid is succinic acid or tartaric acid.

2. A method for preparing the acid addition salt of 1-(5-(2,4-difluorophenyl)-1-((3-fluorophenyl)sulfonyl)-4-methoxy-1H-pyrrol-3-yl)-N-methylmethanamine of claim 1, the method comprising the steps of:
   (a) dissolving 1-(5-(2,4-difluorophenyl)-1-((3-fluorophenyl)sulfonyl)-4-methoxy-1H-pyrrol-3-yl)-N-methylmethanamine and an acid, respectively, in an organic solvent to prepare a 1-(5-(2,4-difluorophenyl)-1-((3-fluorophenyl)sulfonyl)-4-methoxy-1H-pyrrol-3-yl)-N-methylmethanamine solution and an acid solution; and
   (b) mixing the 1-(5-(2,4-difluorophenyl)-1-((3-fluorophenyl)sulfonyl)-4-methoxy-1H-pyrrol-3-yl)-N-methylmethanamine solution and the acid solution and then stirring the mixed solutions.

3. The method of claim 2 for preparing an acid addition salt of 1-(5-(2,4-difluorophenyl)-1-((3-fluorophenyl)sulfonyl)-4-methoxy-1H-pyrrol-3-yl)-N-methylmethanamine, wherein the acid is succinic acid or tartaric acid.

4. The method of claim 2 for preparing an acid addition salt of 1-(5-(2,4-difluorophenyl)-1-((3-fluorophenyl)sulfonyl)-4-methoxy-1H-pyrrol-3-yl)-N-methyl methanamine, wherein the organic solvent is one or more selected from the group consisting of n-hexane, ethyl acetate, butyl acetate, acetonitrile, chloroform, diethyl ether, acetone, methanol, and ethanol.

5. A pharmaceutical composition for the treatment of gastrointestinal injury due to gastrointestinal tract ulcer, gastritis, reflux esophagitis, or *Helicobacter pylori* (*H. pylori*), comprising the acid addition salt of 1-(5-(2,4-difluorophenyl)-1-((3-fluorophenyl)sulfonyl)-4-methoxy-1H-pyrrol-3-yl)-N-methylmethanamine of claim 1.

* * * * *